United States Patent [19]
Vaidyanathan

[11] 4,420,645
[45] Dec. 13, 1983

[54] PROCESS FOR THE NITRATION OF HALOBENZENES

[75] Inventor: Kumbakonam R. Vaidyanathan, Creve Coeur, Mo.

[73] Assignee: Monsanto Company

[21] Appl. No.: 399,637

[22] Filed: Jul. 19, 1982

[51] Int. Cl.$^3$ .............................................. C07C 79/12
[52] U.S. Cl. .................................................. 568/937
[58] Field of Search ............................... 568/937, 938

[56] References Cited

U.S. PATENT DOCUMENTS

| | | | |
|---|---|---|---|
| 3,077,502 | 2/1963 | Leib | 568/937 |
| 3,253,045 | 5/1966 | Sparks | 568/938 X |
| 3,434,802 | 3/1969 | Toischer et al. | 568/937 X |
| 3,979,467 | 9/1976 | Schumacher | 568/937 |

Primary Examiner—Leland A. Sebastian
Attorney, Agent, or Firm—Wendell W. Brooks; Thomas Y. Awalt, Jr.; Arnold H. Cole

[57] ABSTRACT

Nitrohalobenzenes are prepared in two stages by reacting monohalobenzene with nitric acid.

10 Claims, 1 Drawing Figure

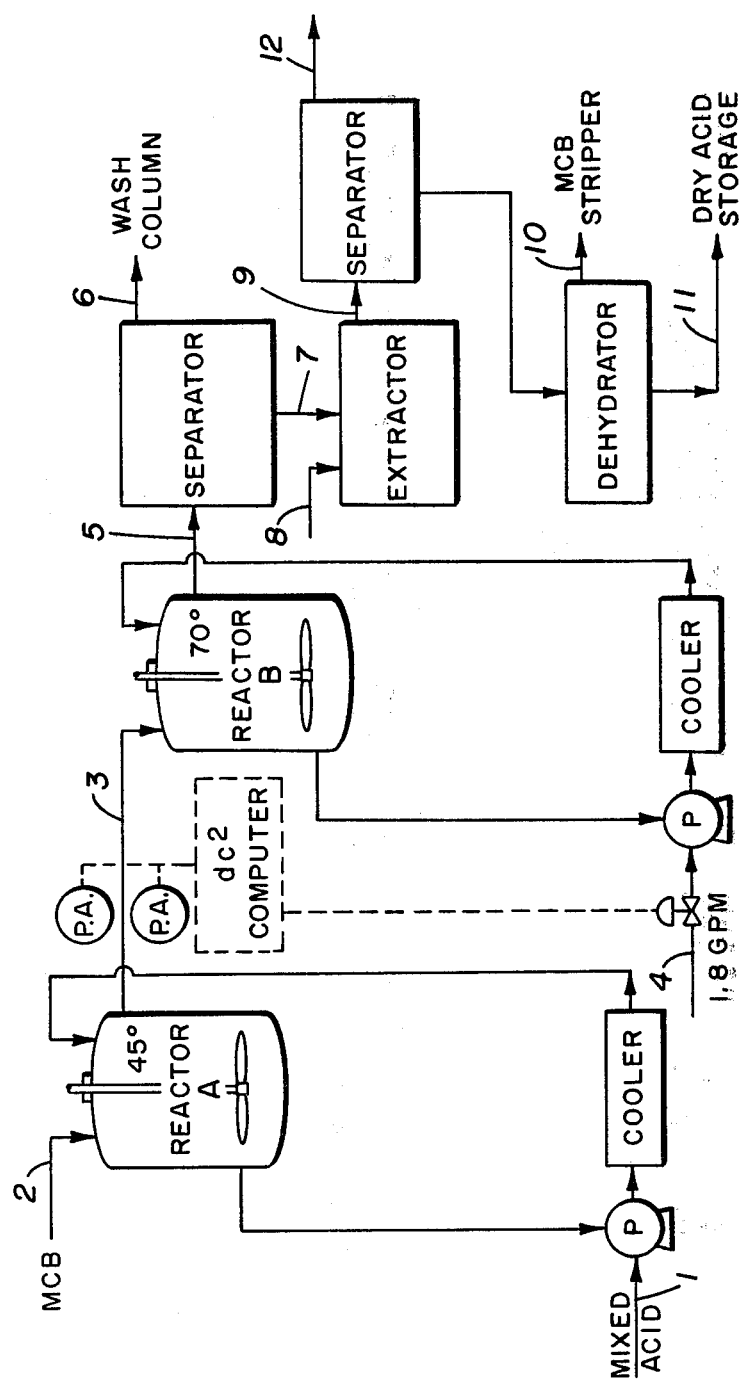

PROCESS FOR THE NITRATION OF HALOBENZENES

BACKGROUND OF THE INVENTION

A. Field of the Invention

The invention relates to an improved process for the preparation of nitrohalobenzenes by the nitration of the corresponding halobenzene.

B. The Prior Art

It is well known to produce nitrohalobenzenes (such as nitrochlorobenzene) from halobenzenes (such as monochlorobenzene) by reacting the halobenzene with nitric acid and a second acid selected from the group consisting of sulfuric acid, phosphoric acid, sulfonic acid and mixtures of the above.

Typical of such processes is that described by U.S. Pat. No. 3,077,502, a commercial translation of which is a three-reactor conversion wherein sulfuric acid and nitric acid, as well as monochlorobenzene, is fed into the first reactor, with heat being removed and temperature maintained at about 45° C. Residence time is about 45 minutes in the first reactor, and the conversion level based on nitric acid is 85–90%. The contents of the first reactor overflow into the second reactor wherein temperature is maintained at about 65° C. Residence time in the second reactor is about 45 minutes, and the conversion level is about 90–95%.

The contents of the second reactor overflow into a third reactor where temperature is maintained at about 70° C. Residence time is about 60 minutes and conversion based on nitric acid is close to about 99.5%.

Sulfuric acid takes up the water generated during the course of the reaction, and its concentration drops from about 85% to about 73.5% at the end of the reaction. The spent acid is removed from the product stream in an oil-acid separator, and is pumped to an acid dehydrator. The dehydrated sulfuric acid at about 85% concentration is returned to the process.

Any method for increasing the efficiency of this production would be a significant advance in the art and is an object of this invention.

SUMMARY OF THE INVENTION

According to the instant invention, nitric acid and one or more of sulfuric acid, phosphoric acid, or sulfonic acid with an excess of monohalobenzene is fed to a first reactor with controlled cooling so as to obtain a conversion of at least about 75% of the nitric acid. The reaction product is fed into a second reactor into which is also continuously fed the one or more of sulfuric acid, phosphoric acid, or sulfonic acid in the amounts stoichiometrically required as of the time of feeding into the second reactor, with controlled cooling so as to obtain a conversion of at least about 98% of the nitric acid.

In the detailed description, reference will be made to the drawing in which the FIGURE is a schematic flow sheet of a preferred embodiment of this invention.

DETAILED DESCRIPTION OF THE INVENTION

In laboratory studies, it was discovered and/or observed that for every mole of monohalobenzene converted one mole of water is generated; that sulfuric acid can take up to two moles of water per mole of sulfuric acid, and that if there is any free water in the reaction, it will tie up the nitric acid and make it unreactive. It has also been observed that the addition of strong sulfuric acid at the end of a batch run drives the reaction to completion.

As indicated above, the invention is an improvement in a continuous process for the production of nitrohalobenzene from monohalobenzene by reacting monohalobenzene with nitric acid and a second acid selected from the group consisting of sulfuric acid, phosphoric acid, sulfonic acid and mixtures of the above. The improvement comprises feeding nitric acid and the second acid and an excess of monohalobenzene to a first reactor with controlled cooling so as to obtain a conversion of at least about 75% of the nitric acid, and continuously feeding the reaction product of the first reactor into a second reactor into which is also continuously fed the proportion of the second acid stoichiometrically required as of the time of feeding the reaction product into the second reactor, with controlled cooling so as to obtain a conversion of at least about 98% of the nitric acid.

In a preferred version, at least 85% of the nitric acid is converted in the first reactor, and at least 99.5% of the nitric acid is converted in the second reactor. In order to determine the amount of acid stoichiometrically required as of the time of feeding into the second reactor, a slip stream from an overflow line from the first reactor may be analyzed. Analysis may be accomplished by monitoring the specific gravities of the separate components of the slip stream (by using a nuclear densitometer). The slip stream may be separated by an oil-acid separator, as is well known in the art. A concentration of the second acid as the reaction product leaves the first reactor is preferably about 75%; and after the addition of the second acid to the second reactor, its concentration is preferably about 77.5%. Preferably the temperature of the first reactor is maintained at about 45° C.; and the temperature of the second reactor is maintained at about 70° C.

While the invention is directed to the production of all nitrohalobenzenes from halobenzenes it will be described in detail in terms of nitrochlorobenzene from monochlorobenzene.

Referring now in detail to the FIGURE, reactor A is fed by mixed acid stream 1 and monochlorobenzene stream 2. Mixed acid stream 1 is a recirculating stream through a cooler, regulated to maintain the temperature in reactor 1 at about 45° C. The overflow from reactor A is stream 3 based on an 85% conversion to nitrochlorobenzene based on consumption of nitric acid. Stream 3 is constantly monitored so as to determine the amount of sulfuric acid to be added in stream 4 to be stoichiometrically required to complete the reaction in reactor B. Reactor B is maintained at 70° C. The product stream 5 from reactor B is fed to a first separator which removes most of the nitrochlorobenzene from the stream, feeding it through stream 6 to a wash column. Stream 7, comprising the remainder of the product stream, is fed to an extractor into which is fed monochlorobenzene via stream 8 and out of which is drawn stream 9 into a second separator from which is drawn stream 2 comprised primarily of monochlorobenzene for feed to reactor 1. The residue from the second separator is fed to a dehydrator from which is drawn primarily water at stream 10 and sulfuric acid at stream 11.

EXAMPLES

1. Production of nitrochlorobenzene as described above was conducted according to and with the results shown at Table 1. Stream components are designated in FIG. 1.

TABLE 1

| STREAM COMPONENT | (1) | (2) | (3) 85% Conv. On Nitric | (4) | (5) 99.5% Conv. On Nitric | (6) | (7) | (8) | (9) | (10) | (11) |
| --- | --- | --- | --- | --- | --- | --- | --- | --- | --- | --- | --- |
| Nitric Acid | 7,024 | — | 1,054 | — | 35 | 17 | 18 | — | 3 | 3 | — |
| Sulfuric Acid | 11,184 | — | 11,184 | 1,585 | 12,769 | 13 | 12,756 | — | 12,756 | — | 12,756 |
| Water | 1,974 | — | 3,680 | 32 | 4,003 | 3 | 4,000 | — | 4,004 | 1,753 | 2,251 |
| MCB | — | 13,484 | 2,834 | — | 1,014 | 1,014 | — | 13,630 | 13,603 | 109 | — |
| NCB | — | 136 | 15,060 | — | 17,608 | 17,408 | 200 | — | 237 | 101 | — |
| TOTAL | 20,182 | 13,630 | 33,812 | 1,617 | 35,429 | 18,455 | 16,974 | 13,630 | 30,603 | 1,966 | 15,007 |
| Temperature (°C.) | | | 45 | | 70 | | | | | | |
| Comment: Addition of 98% H2SO4 | | | | 1.3 gpm | | | 20 gpm | | | | |

2. Following the same process, and with the same conditions and reactions as shown at Table 2, the reaction was conducted with the results also shown at Table 2.

TABLE 2

| STREAM COMPONENT | (1) | (2) | (3) 85% Conv. On Nitric | (4) | (5) 99.5% Conv. On Nitric | (6) | (7) | (8) | (9) | (10) | (11) |
| --- | --- | --- | --- | --- | --- | --- | --- | --- | --- | --- | --- |
| Nitric Acid | 7,024 | — | 1,054 | — | 35 | 17 | 18 | — | 3 | 3 | — |
| Sulfuric Acid | 11,184 | — | 11,184 | 3,804 | 14,988 | 15 | 14,973 | — | 14,973 | — | 14,973 |
| Water | 1,974 | — | 3,680 | 671 | 4,642 | 4 | 4,638 | — | 4,642 | 2,000 | 2,642 |
| MCB | — | 13,494 | 2,834 | — | 1,014 | 1,014 | — | 13,630 | 13,603 | 109 | — |
| NCB | — | 136 | 15,060 | — | 17,608 | 17,408 | 200 | — | 237 | 101 | — |
| TOTAL | 20,182 | 13,630 | 33,812 | 4,475 | 38,287 | 18,458 | 19,829 | 13,630 | 33,458 | 2,213 | 17,615 |
| Temperature (°C.) | | | 45 | | 70 | | | | | | |
| Comment: Addition of 85% H2SO4 | | | | 5 gpm | | | 23.3 gpm | | | | |

I claim:

1. In a continuous process for the production of nitrohalobenzene from monohalobenzene by reacting monohalobenzene with nitric acid and a second acid selected from the group consisting of sulfuric acid, phosphoric acid, sulfonic acid and mixtures of the above, the improvement comprising:
   (1) feeding nitric acid, the second acid and an excess over the stoichiometrically required monohalobenzene to a first reactor with controlled cooling so as to obtain a conversion of at least about 75% of the nitric acid, and
   (2) continuously feeding the reaction product of (1) into a second reactor into which is also continuously fed the proportion of the second acid stoichiometrically required as of the time of feeding the reaction product of (1) into the second reactor, with controlled cooling so as to obtain a conversion of at least about 98% of the nitric acid.

2. The process of improvement of claim 1 wherein the conversion of nitric acid in the first reactor is at least about 85% and the conversion of nitric acid in the second reactor is at least about 99.5%.

3. The process improvement of claim 1 wherein the proportion of the second acid stoichiometrically required as of the time of feeding the reaction product of (1) into the second reactor is continuously determined by analysis of a slip stream from an overflow line from the first reactor.

4. The process improvement of claim 3 wherein before analysis thereof, the slip stream is separated by an oil-acid separator.

5. The process improvement of claim 4 wherein the analysis is accomplished by monitoring the specific gravities of the separated components of the slip stream.

6. The process improvement of claim 1 wherein the concentration of sulfuric acid leaving the first reactor is about 75%.

7. The process improvement of claim 1 wherein after the addition of the second acid to the second reactor, the concentration of sulfuric acid is about 77.5%.

8. The process improvement of claim 1 wherein the temperature in the first reactor is about 45° C.

9. The process improvement of claim 1 wherein the temperature in the second reactor is about 70° C.

10. The process improvement of claim 1 wherein the monohalobenzene is monochlorobenzene and the nitrohalobenzene is nitrochlorobenzene.

* * * * *